United States Patent [19]

Masuho et al.

[11] 4,368,149

[45] Jan. 11, 1983

[54] PROTEIN HYBRID HAVING CYTOTOXICITY AND PROCESS FOR THE PREPARATION THEREOF

[75] Inventors: Yasuhiko Masuho, Hino; Takeshi Hara, Hachioji, both of Japan

[73] Assignee: Teijin Limited, Osaka, Japan

[21] Appl. No.: 331,342

[22] Filed: Dec. 16, 1981

[30] Foreign Application Priority Data

Dec. 22, 1980 [JP] Japan .................................. 55-180553

[51] Int. Cl.$^3$ ......................... A61K 39/44; C07G 7/00
[52] U.S. Cl. ................................... 260/112 B; 424/85; 424/88
[58] Field of Search .................... 260/112 B; 424/851, 424/88

[56] References Cited

U.S. PATENT DOCUMENTS

| | | | |
|---|---|---|---|
| 4,046,722 | 9/1977 | Rowland | 260/112 B X |
| 4,093,607 | 6/1978 | Sela et al. | 260/112 B |
| 4,315,851 | 2/1982 | Yoshikumi et al. | 260/112 B |

OTHER PUBLICATIONS

Archives of Biochemistry & Biophysics, 169, 522–528 (1975), Irvin.
J. Natl. Cancer Inst., vol. 61, pp. 657–676, 1978, Ghose et al.
Biochemical Biophysical Res. Commun. vol. 90, pp. 320–360, 1979, Masuho et al.
Biochemical Journal, vol. 186 (Feb. 1980), pp. 443–452, Barbieri et al.

Primary Examiner—Howard E. Schain
Attorney, Agent, or Firm—Sughrue, Mion, Zinn, Macpeak & Seas

[57] ABSTRACT

A protein hybrid having cytotoxicity obtained by covalently bonding an immunoglobulin or its fragment, which is capable of binding selectively to an antigen possessed by a cell to be destroyed, to a protein, which is obtained from *Momordica charantia* and has an activity to terminate protein synthesis. This protein hybrid displays remarkable cytotoxicity against targel cells.

7 Claims, 4 Drawing Figures

PROTEIN HYBRID HAVING CYTOTOXICITY AND PROCESS FOR THE PREPARATION THEREOF

BACKGROUND OF THE INVENTION

1. Field of the Invention

The present invention relates to a novel protein hybrid having cytotoxicity and a process for the preparation thereof. More particularly, the present invention relates to a novel protein hybrid having cytotoxicity comprising a constituent part consisting of an immunoglobulin capable of bonding selectively to a specific antigen possessed by a cell to be killed (hereinafter referred to as a target cell) or consisting of a fragment having a part which binds to such antigen and a constituent part consisting of a protein (hereinafter referred to as MOM) which is a purified extract of *Momordica charantia* (bitter pear melon) capable of inhibiting protein synthesis and a process for the preparation of the same.

2. Description of the Prior Art

Attempts and trials have heretofore been made to bond an immunoglobulin, which is capable of binding selectively to a target cell, with a variety of cytotoxic substances with the purpose of destroying certain kinds of cells selectively. As cytotoxic substances to be bonded to the immunoglobulin, antitumor drugs, enzyms, or toxins have so far been used (Refer to T. Ghose et al., J. Natl. Cancer Inst., Vol. 61, pp. 657–676, 1978). However, since these substances essentially have nonselective cytotoxicity, sufficient selective toxicity is not expected of them when they are coupled to a specific immunoglobulin. The inventors of the present invention have recently succeeded in obtaining a protein hybrid having outstanding selective toxicity by first separating fragment A, which has a lethal activity by inhibiting protein synthesis, and fragment B which binds to a variety of cells nonselectively, from diphtheria toxin and then by cross-linking said fragment A and fragment Fab' of immunoglobulin (refer to Y. Masuho et al., Biochem. Biophys. Res. Commun., Vo. 90, pp. 320–360, 1979 and Japanese Patent Application Laid-Open No. 136,235/80). It is known that, besides diphtheria toxin, fragments having an activity to inhibit protein synthesis can be obtained from plant toxin ricin, abrin, modeccin, etc. (refer to Japanese Patent Application Laid-Open No. 49,321/80, for instance). A hybrid of fragment of such toxin and immunoglobulin or its fragment has a few demerits since it uses protein arising from toxin.

The first of such demerits is that it is difficult to obtain pure fragments having an activity to inhibit protein synthesis. The second is a problem, which somewhat relates to the first one, that intact toxin is apt to come into the fragment thus making the cytotoxicity of the hybrid nonselective destroying not only target cells but also other cells due to the extremely strong cytotoxicity of the toxing even if the amount of toxin coming into the fragment is very small.

SUMMARY OF THE INVENTION

The present invention is directed to a protein hybrid having cytotoxicity, which is obtained by covalently bonding an immunoglobulin or its fragment capable of binding to a specific antigen possessed by a cell to be killed, to a protein (MOM) which is obtained from *Momordica charantia* and capable of inhibiting protein synthesis and also to a process for preparing a protein hybrid having cytotoxicity which comprises linking an immunoglobulin or its fragment with MOM by use of a cross-linking agent.

MOM of *Momordica charantia* to be used in the present invention can hardly enter into cells by itself; therefore it can exert a toxic action very sparingly. However, MOM has an especial feature in that it can be isolated and purified very easily, since it can be used without being fragmented. And the protein hybrid of the present invention has an functional effect to send said MOM into target cells selectively.

The present invention accordingly offers a protein hybrid having cytotoxity endowed with very high selectivity, free from demerits found with prior arts.

DESCRIPTION OF THE PREFERRED EMBODIMENTS

Figure 1:
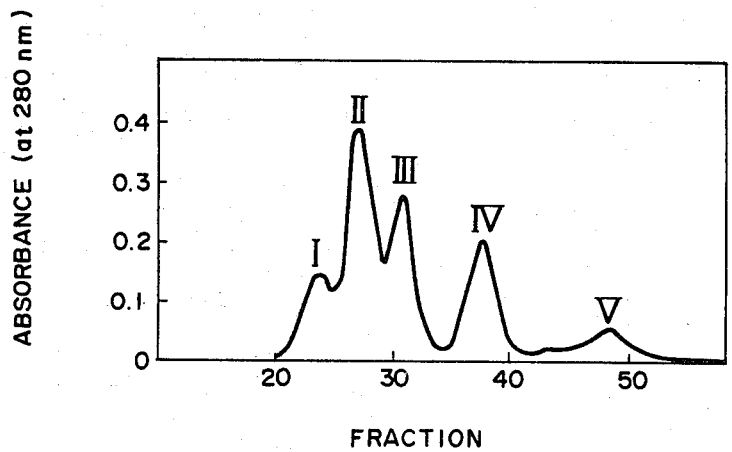
FIG. 1 is a protein elution pattern obtained by Sephadex G150 (superfine) column chromatography conducted for the reaction mixture prepared in Example 1, (f).

In the present invention, what is referred to as an immunoglobulin (a leading part of the protein hybrid having cytotoxicity) which is capable of binding selectively to a specific antigen of a cell to be killed includes the following. It is an immunoglobulin prepared from antisera isolated from animals such as man, monkey, horse, cow, goat, sheep, rabbit, guinea pig, hamster, rat, mouse, etc. which are immunized with such target cells as tumor cells or certain lymphocytes or tissues which contain any of them by such a publicly known method as ethanol fractionation, ammonium sulfate fractionation, ion exchange, and molecular sieve column chromatography. It is also a monoclonal antibody obtained fom antibody-producing lymphocytes transformed by a carcinogen such as carcinogenic virus or from hybridomas which are prepared by allowing antibody-producing lymphocytes obtained from an animal immunized with the target cells to fuse with myeloma cells. An immunoglobulin, which is obtained by cleaving its binding to the target cell by use of a surface active agent, etc. and is specific to said target cell, is also included in the immunoglobulins of the present invention.

It is known that the immunoglobulin falls under five classes, i.e. IgG, IgA, IgM, IgD, and IgE, and each class consists of several subclasses. But they are identical in their basic structure in that they consist of two heavy chains and two light chains and that they are composed of Fab moieties which have an activity of binding to an antigen and an Fc moiety which has an effector activity. However, IgM exists as a pentamer and IgA partially as a dimer and it is desirable from the viewpoint of tissue permeability of the cytotoxic protein hybrid to reduce them to monomers with mercaptan prior to use as a leading part of the hybrid.

As a leading part of the cytotoxic protein hybrid, the whole of the immunoglobulin may be used, but it is preferable to use a fragment which has an antigen binding part but not an Fc part. This is because in the hybrid, which contains an Fc part in it, the Fc part encourages non-specific adsorptive binding to cells other than target cells and the binding with an Fc receptor on the cell membrane, thus reducing the capability of the cytotoxic protein hybrid to select cells to be killed. Furthermore, since the antigenecity of the immunloglobulin as a xenogeneic protein is especially strong at its Fc part, a fragment of the immunoglobulin having no Fc part is preferable to be used as a leading part of the cytotoxic protein hybrid from viewpoint of lowering the antigenecity of the protein hybrid. The decomposition of an immunoglobulin with a proteolytic enzyme such as papain, trypsin, chymotrypsin, plasmin, etc. generally gives what is called Fab fragment having one variable region. Also the peptic decomposition, or the tryptic decomposition depending upon the conditions, of an immunoglobulin gives what is called F(ab')₂ fragment having two variable regions. This fragment further turns to a monovalent Fab' fragment when it is treated with mercaptan. When the immunoglobulin is decomposed while being denatured, it gives a variable region only. These fragments arising from immunoglobulins can all be used as a leading part of the protein hybrid of the present invention disregard of the class and subclass to which the material globulins belong.

What is called MOM, a protein capable of inhibiting protein synthesis obtained from *Momordica charantia,* in the present invention is a protein, which has the molecular weight of about 23,000, can be extracted from the seeds of *Momordica charantia* and purified according to a generally known method, such as the method proposed by L. Barbieri et al., (Biochem. J. Vol. 186, pp. 443–452, 1980) and has a strong activity to inhibit the protein synthesis of rabbit recticulocyte lysate.

The protein hybrid having cytotoxicity of the present invention is prepared by covalently cross-linking an immunoglobulin or its fragment and PAP obtained from *Momordica charantia.* This kind of cross-linking by means of covalent bonding may be effected by directly binding both constituent elements by amide linkage with the use of a carbodiimide reagent such as dicyclohexylcarbodiimide (DCC), 1-ethyl-3-(3-dimethylaminopropyl)carbodiimide hydrochloride (EDCI), etc. as a condensing agent. Also both constituent elements may be linked with the use of a cross-linking reagent having a plural number of the same cross-linking functional groups in the molecule. Glutaraldehyde, toluenediisocyanate, 2,2'-dicarboxy-4-4'-azophenylenediisocyanate, diethylmalonimidate hydrochloride, for instance, may be mentioned as a cross-linking agent for such a use. A hybrid can be prepared by covalently bonding an immunoglobulin or its fragment with MOM according to the methods mentioned above; however, it is difficult to obtain a desired hybrid, because there also occur intramolecular cross-linking, cross-linking between immunoglobulins or their fragments, or cross-linking between MOM's. Therefore, a preferable method is one in which firstly one of the constituent elements, i.e. an immunoglobulin or its fragment and MOM, is made to react with a cross-linking agent with the use of a cross-linking reagent which has a several number (preferably one each) of two kinds of cross-linking functional groups different from each other in the molecule, and then the reaction product thus obtained is made to react with the other of the constituent elements. In this case, the abovementioned reaction can be carried out after cross-linking functional groups are introduced to both or either of the constituent elements.

Under the method mentioned above, the protein hybrid having cytotoxicity expressed by formula (I) or (II) can be obtained:

$$Ab\!-\!\!(\!X_1\!)_t\!-\!MOM)_n \qquad (I)$$

$$(Ab\!-\!(X_1)_t)_n MOM \qquad (II)$$

(where Ab expresses an immunoglobulin or its fragment; MOM indicates a protein having an activity to inhibit protein synthesis obtained from *Momordica charantia;* $X_1$ is a divalent organic group; t stands for 0 or 1; and n indicates an integer of 1 to 3).

$X_1$ is a divalent organic group arising from a cross-linking agent; however, of the cytotoxic protein hybrids, those hybrids expressed by the following formulas (III), (IV), (V), and (VI) are especially preferable from the viewpoint of preparation, separation, purification, and activation:

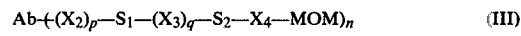

$$Ab\!-\!\!(\!X_2\!)_p\!-\!S_1\!-\!(X_3)_q\!-\!S_2\!-\!X_4\!-\!MOM)_n \qquad (III)$$

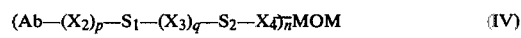

$$(Ab\!-\!(X_2)_p\!-\!S_1\!-\!(X_3)_q\!-\!S_2\!-\!X_4)_n MOM \qquad (IV)$$

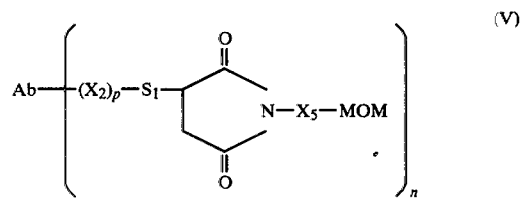

(V)

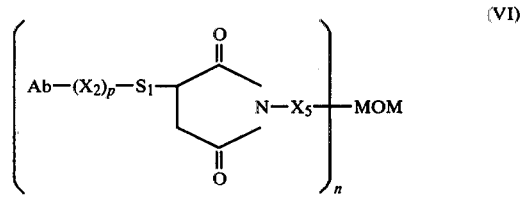

(VI)

(where definitions of Ab, MOM, and n are the same as those given in cases of formulas (I) and (II); $X_2$, $X_3$, $X_4$, and $X_5$ indicate divalent organic groups, $S_1$ and $S_2$ stand for sulfur atoms; p and q are the same or different from each other, indicating 0 or 1).

In the abovementioned formulas (III) to (VI), when p=0, $S_1$ is a sulfur atom arising from an immunoglobulin or its fragment and when p=1, $S_1$ is a sulfur atom introduced by a cross-linking agent. $S_2$ is a sulfur atom introduced by a cross-linking agent. In formulas (III)

and (IV), when q=0, sulfur atoms $S_1$ and $S_2$ link together directly to form a disulfide group. On the other hand, when q=1, sulfur atoms $S_1$ and $S_2$ link together through the medium of $X_3$, a divalent organic group. $X_3$ is a divalent organic group arising from a cross-linking agent having two functional groups which react with a thiol group, for instance, a cross-linking agent expressed by formula (VII):

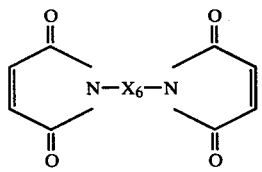
(VII)

(where $X_6$ is a divalent organic group) or benzoquinone.

$X_2$ in formulas (III) to (VI) and $X_4$ in formulas (III) and (IV) are the same or different from each other and are divalent organic groups arising respectively; from a cross-linking agent expressed by the following formula (VIII):

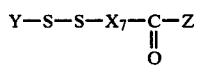
(VIII)

(where Y indicates a monovalent organic group which can form an active disulfide group together with a sulfur atom S linked to it; $X_7$ is a divalent organic group; and Z indicates an alcohol residue of active ester), from a cross-linking agent expressed by the following formula (IX):

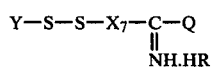
(IX)

(where definitions of Y and $X_7$ are the same as those given in case of formula (VIII); Q indicates an alcohol residue of imido ester; and R represents a halogen atom), from a cross-linking agent expressed by the following formula (X):

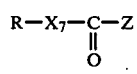
(X)

(where definitions of $X_7$ and Z are the same as those given in case of formula (VIII) and a definition of R is the same as that given in case of formula (IX)), from a cross-linking agent (2-iminothiolactone) expressed by the following formula (XI):

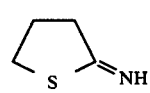
(XI)

from a cross-linking agent (N-acetylhomocystine) expressed by the following formula (XII):

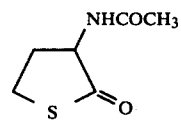
(XII)

from a cross-linking agent (S-acetylmercaptosuccinic acid anhydride) expressed by the following formula (XIII):

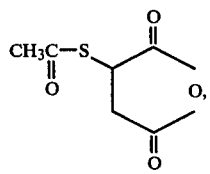
(XIII)

and from a cross-linking agent expressed by the following formula (XIV):

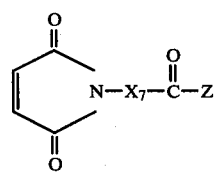
(XIV)

(where definitions of $X_7$ and Z are the same as those given in case of formula (VIII)).

As concrete examples of monovalent organic groups which are able to form an active disulfide group together with a linked sulfur atom, a 2-pyridyl group

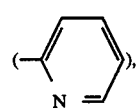

4-pyridyl group

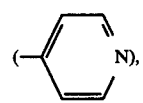

3-carboxy-4-nitrophenyl

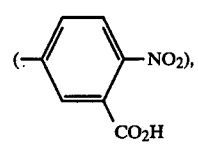

etc. may be mentioned. There are no restrictions as to the kind of a divalent organic group expressed by $X_6$ or $X_7$ so far as it is chemically inactive; however, in general, it is suitably selected from among alkylene groups or phenylene groups, both having branchings or not. As concrete examples of alcohol residue of active ester expressed by Z, 2,4-dinitrophenoxy group

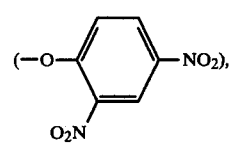

succinimidoxy group

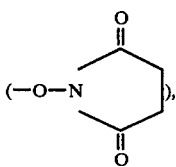

etc. may be mentioned. As concrete examples of alcohol residue of imido ester expressed by Q, methoxy group, ethoxy group, etc. may be mentioned. As concrete examples of halogen atom expressed by R, chlorine, bromine, etc. may be mentioned.

As concrete examples of cross-linking agent, N,N'-(1,2-phenylene)dimaleimide, N,N'-(1,4-phenylene)-dimaleimide, 4,4'-bis(maleoylamino)azobenzene, and bis(N-maleimidomethyl)ether may be mentioned as cross-linking agent expressed by formula (VII); N-succinimidyl 3-(2-pyridyldithio)propionate, and or Pro 1 is made to react with a cross-linking agent expressed by formula (XI) or (XII) to form a protein expressed by formula (XVIII) or formula (XIX), or with a cross-linking agent expressed by formula (XIII) followed by deacetylation of the resulting protein in form a protein expressed by formula (XX), and thus obtained protein is then treated with a reagent which converts a thiol group into an active disulfide group, such as 2,2'-dipyridyldisulfide

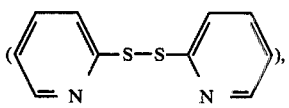

4,4'-dipyridyldisulfide

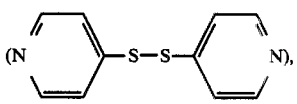

and 5,5'-dithiobis(2-nitrobenzoic acid)

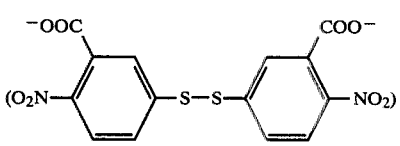

(reaction (4), (5) or (6))

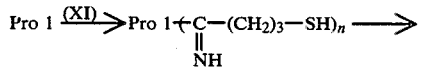

(XVIII)

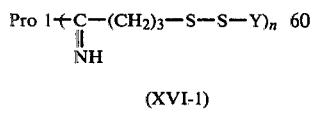

(XVI-1)

(where a definition of Y is the same as that in case of formula (VIII)), 2,4-dinitrophenyl 3-(4-pyridyldithio)-propionate as cross-linking agent expressed by formula (VII); methyl 3-(2-pyridyldithio)propionimidate hydrochloride as cross-linking agent expressed by formula (IX); and n-succinimidyl 3-bromopropionate as cross-linking agent expressed by formula (X).

Of the cytotoxic protein hybrids of the present invention, the hybrid expressed by formula (III) or (IV) can be prepared according to the method in which active disulfide is introduced to either of the immunoglobulin or its fragment and MOM which form the protein hybrid (hereinafter the optional one protein shall be referred to as Pro 1 and the other protein Pro 2) and a thiol group is introduced to or formed in the other and then both proteins are cross-linked by means of disulfide bond or by use of a cross-linking agent. More particularly, Pro 1 is made to react with a cross-linking agent expressed by formula (VIII) or formula (IX) (reactions (1) and (2))

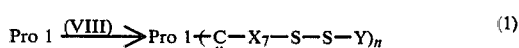

(XV)

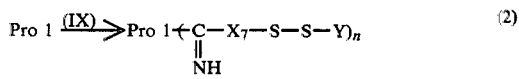

(XVI)

or is made to react with a cross-linking agent expressed by formula (X), followed by the thiosulfite ion treatment of the reaction product (XVII) (reaction 3)

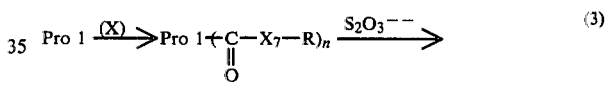

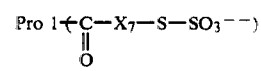

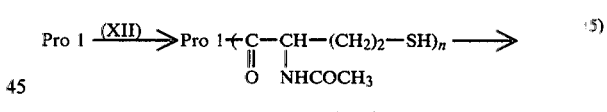

(XIX)

(XV-2)

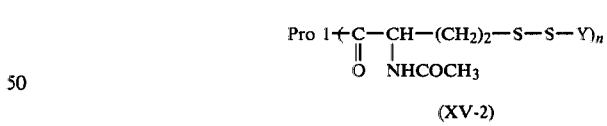

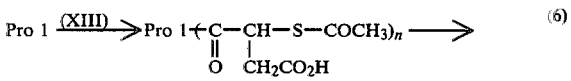

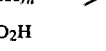

(XX)

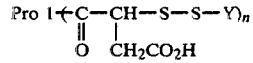

(XV-3)

to obtain Pro 1 (a protein expressed by formula (XV), (XVI), (XV-1), (XVI-1), (XV-2), or (XV-3) to which an active disulfide group is introduced). On the other hand, a disulfide group of protein, expressed by the following formula (XXI), (XXIII), or (XXI-1) which is prepared from the other protein Pro 2 according to the above-mentioned formula (1), (2), or (3), and to which a disulfide group is introduced, is reduced with such a thiol reagent as 2-mercaptoethanol, dithiothreitol, etc., (reaction (7), (8), or (9))

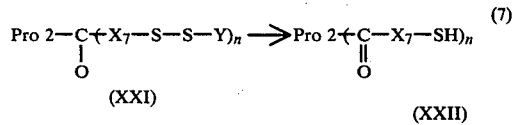

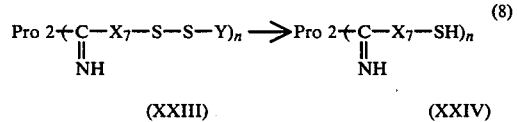

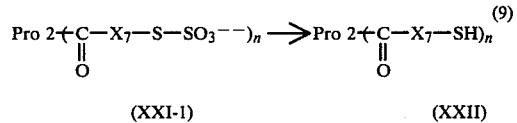

or Pro 2 is subjected to the first step of the reaction expressed by formula (4) or (5) or to the first and second steps of the reaction expressed by formula (6), to obtain Pro 2 to which a thiol group is introduced (a protein expressed by formula (XXII), (XXIV), (XXIV-1), (XXII-1) or (XXII-2)

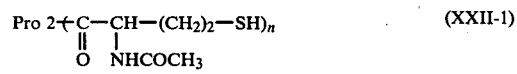

(In the foregoing, $X_7$ in the formula (XV), (XVI), or (XV-1) and $X_7$ in formula (XXII) or (XXIV) may be the same or different from each other.) The cytotoxic protein hybrid of the present invention expressed by formula (III) or (IV) (in both cases q=0) can be prepared by making Pro 2, which is obtained by the introduction of a thiol group as mentioned above, react with Pro 1 which is likewise obtained by the introduction of an active disulfide group as mentioned above.

A protein hybrid of the present invention expressed by formula (V) or (VI) can be prepared by first making MOM react with a cross-linking agent expressed by formula (XIV), for instance, to obtain a protein to which a maleimide group expressed by formula (XXV) is introduced,

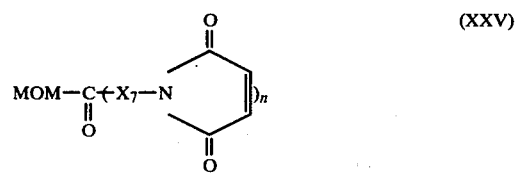

and then making thus obtained protein react with an immunoglobulin or its fragment to which a thiol group is prepared according to the reaction formula (7), (8), (9), the first step of the reaction formula (4) or (5) or the first and second steps of the reaction formula (6).

One of the precursors of the protein hybrid of the present invention expressed by formula (III), (IV), (V), or (VI) is a protein having a thiol group. The thiol groups as these may include, in addition to a thiol group introduced from outside as mentioned concretely with the chemical formulas, a thiol group of the protein itself when the protein has one or a thiol group obtained by reducing the disulfide bond of the protein arising from a cysteine group.

In the aforementioned cross-linking reaction between an immunoglobulin or its fragment and MOM, it is desirable to use 1 to 100 moles of a cross-linking agent per 1 mole of protein to react with in case an immunoglobulin or its fragment is made to react with a cross-linking agent or in case MOM is made to react with a cross-linking agent. The reaction is conducted by adding an aqueous solution of cross-linking agent or a solution prepared by dissolving a cross-linking agent in a small amount of organic solvent such as N,N-dimethylformamide, dimethylsulfoxide, 1,2-dimethoxyethane, methanol, ethanol, acetone, etc. when the cross-linking agent is insoluble in water, to a solution prepared by dissolving an immunoglobulin or its fragment, or MOM in such a way that the concentration of protein in the buffer with pH adjusted to 4–9 may be in the range of 0.5–100 mg/ml (more preferably in the range of 1–20 mg/ml) at 0° to 50° C. with stirring. The reaction time varies depending upon the reaction scale and reaction conditions and, in general, the reaction is carried out within 2 days. After the reaction is over, the cross-linking agent left unreacted is removed by dialysis or molecular sieve column chromatography to obtain a solution of protein to which the cross-linking agent is introduced. A solution prepared by dissolving a protein, which is another constituent element of the hybrid (or a protein to which a cross-linking functional group is introduced by a cross-linking agent) in a buffer with the pH value of 4–9 (the preferable range of protein concentration is the same as those mentioned above) is made to react at 0° to 50° C. The separation of the hybrid from the reaction mixture and its purification can be carried out following the ordinary procedure such as molecular sieve column chromatography. The hybrid can also be prepared by adding a solution of a protein, which makes one of the constituent elements of the hybrid and to which a cross-linking agent is introduced, to a solution of a protein which makes another of the constituent elements of the hybrid. Furthermore, the reaction conditions to be adopted in the following cases are the same as the reaction conditions adopted in the above-mentioned case where a cross-linking agent is made to react with a protein; in case where a protein, to which a cross-linking agent is introduced, is treated with a low molecular weight reagent to be coverted to a protein having a specific cross-linking functional group (for instance, in case where an active disulfide group introduced by a cross-linking agent is converted into a thiol group), or in case where an immunoglobulin or its fragment or MOM is directly converted into an activated derivative with the use of a low molecular weight reagent (for instance, in case where a thiol group of fragment Fab' of the immunoglobulin is converted into an active dissulfide).

The present invention is described in detail by the following examples.

EXAMPLE 1

(a) Extraction of protein (MOM) having activity to inhibit protein synthesis from seeds of Momor Momordica charantia and purification thereof 9.2 g of the seeds of Momordica chrantia was thoroughly ground down in a motor with a pestle and had its lipid removed by use of ether. 50 ml of 5 mM phosphate buffer—0.2 M sodium chloride solution (pH 7.2) was added to thus obtained lipid-free powder and the mixture was stirred at 40° C. overnight. Thereafter, insoluble substances remaining in the solution were removed by centrifugation and ammonium sulfate was added thereto to give 30% saturation. The mixture was stirred at 0° C. for 1 hour and the supernatant was collected by centrifugation. Ammonium sulfate was further added to the supernatant to give 70% saturation and the mixture was stirred at 0° C. for 2 hours. The precipitate was separated by centrifugation. The obtained precipitate was dissolved in 5 ml of 5 mM phosphate buffer (pH 6.5) and the solution was thoroughly dialyzed against the same 5 mM phosphate buffer. The dialyzate was subjected to Sephadex G 150 (superfine) column chromatography (column size 84 cm×2.5 cm) equilibrated with the same 5 mM phosphate buffer and the fractions of effluent protein at the site of molecular weight of about 30,000 was pooled. This pool was put to CM Sephadex C-50 column chromatography (column size 1.6 cm×34 cm). The resin was equilibrated with 5 mM phosphate buffer (pH 6.5). When the salt concentration was raised in the order of 0.05 M phosphate buffer (pH 6.5), 0.1 M phosphate buffer (pH 6.5), and 0.2 M phosphate buffer (pH 6.5), MOM started to effuse at the salt concentration of 0.1 M. It was confirmed that the protein of this fraction had molecular weight of about 27,000 and that the fraction did not contain other proteins as shown by sodium dodecyl sulfate-polyacrylamide gel electrophoresis (hereinafter referred to as SDS-PAGE). SDS-PAGE was carried out according to a method of K. Weber and M. Osborn (Journal of Biological Chemistry, Vol.244, pp.4406–4412, 1969).

(b) Preparation of N-[3-(2-pyridyl)dithiopropionyl]MOM 0.05 ml of ethanol solution containing 9 mM N-succinimidyl 3-(2-pyridylthio)propionate (SPDP) was added to 1.4 ml of 0.02 M phosphate buffer—0.14 M sodium chloride—1 mM ethylenediaminetetraacetic acid (hereinafter referred to as EDTA) solution (pH 7.5) containing 3.8 mg of MOM extracted and purified according to the preceding (a) and the mixture was made react at room temperature for 30 minutes. The reaction product was put to Sephadex G25 column chromatograph on said phosphate buffer (pH 7.5) to remove the excess reagent. MOM, into which about 2 N-[3-(2-pyridyl)dithiopropinyl] groups on the average were introduced, was thus obtained.

(c) Preparation of immunoglobulin against mouse leukemia L 1210 cells

Mouse leukemia L 1210 cells transplanted successively on DBA/2Cr mice were taken out of the ascites of a DBA/2Cr mouse. An emulsion prepared from about $10^8$ of those cells and Freund's complete adjuvant was intravenously injected into rabbits. After that $10^6$ L 1210 cells, together with the adjuvant, were subcutaneously injected three times at intervals of one week, and the rabbits were bled seven to ten days after the day of final injection. The portions of blood thus obtained were mixed, and serum was separated and heated at 56° C. for 30 minutes for inactivation. 200 ml of a saturated aqueous solution of ammonium sulfate was added to 200 ml of thus obtained anti-L 1210 autiserum and the resulting precipitate was separated by means of centrifugation. The precipitate thus separated was dissolved in 50 ml of 0.01 M phosphate buffer (pH 7.6) and was further dialyzed against the same buffer. The dialyzate was put to DEAE cellulose column chromatography (column size 3 cm×94 cm) equilibrated with the same buffer to obtain a solution containing anti-L 1210 IgG as an unadsorbed fraction.

Figure 4:
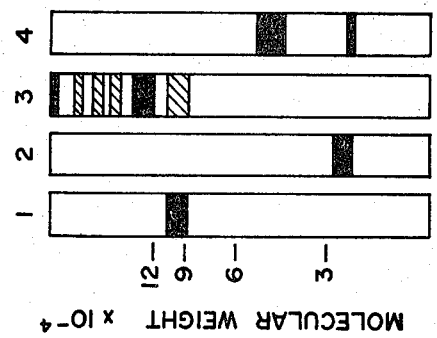
FIG. 4 shows SDS-PAGE patterns obtained with a 6% gel. Disc 1 shows F(ab')$_2$, disc 2 MOM, disc 3 a hybrid of F(ab')$_2$ and MOM obtained in Example 4, (b), disc 4 a reduction product of said hybrid with the use of 2-mercaptoethanol. Portions shaded with oblique lines are bands of low concentration.

(d) Separation of fragment F(ab')$_2$ from immunoglobulin 1.2 g of anti-L 1210 IgG obtained in the preceding (c) was dissolved in 40 ml of 0.1 M acetate buffer (pH 4.5), to which 24 mg of pepsin was added to effect peptic digestion at 37° C. for about 18 hours. The digestion product was put to Sephadex G200 column chromatography (column size 3.5 cm×140 cm) over saline to take out a protein eluted at molecular weight of about 100,000. It was confirmed that this was a pure fragment F(ab')$_2$ by SDS-PAGE as shown in FIG. 4, disc 1.

(e) Preparation of fragment Fab'

0.01 ml of 150 mM aqueous 2-mercaptoethanol solution was added to 1.0 ml of 0.01 M tris.hydrochloride—0.14 M sodium chloride—2 mM EDTA solution (pH 8.3) containing 13.0 mg of fragment F(ab')$_2$ obtained in the preceding (d) and the mixture was subjected to the reduction at 35° C. for 1 hour. After the reaction was over, the solution was put to Sephadex G25 column chromatography (column size 1.0 cm×20 cm) equilibrated with 5 mM acetate buffer—0.14 M sodium chloride—1 mM EDTA solution (pH 5.5) (hereinafter referred to as ANE buffer) to remove 2-mercaptoethanol, thus giving fragment Fab' having 1 thiol group (Refer to FIG. 2, disc 1).

Figure 2:
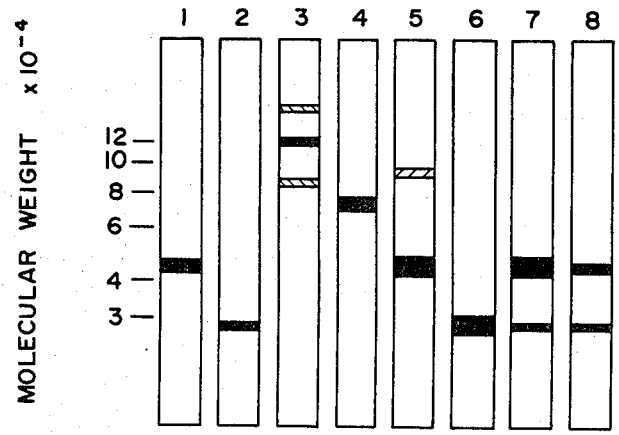
FIG. 2 shows Sodium dodesylsulfate-polyacrylamide gel electrophoresis (hereinafter referred to as SDS-PAGE) patterns obtained with a 6% gel. Disc 1 shows Fab', disc 2 MOM, disc 3 peak I of FIG. 1, disc 4 peak II of FIG. 1, disc 5 peak III of FIG. 1, disc 6 peak IV of FIG. 1, disc 7 a reduction product of peak I of FIG. 1, and disc 8 a reduction product of peak II of FIG. 1. Portions shaded with oblique lines are bands of low concentration.

(f) Preparation of hybrid of fragment Fab' and MOM covalently bonded with bonds containing disulfide bond 3.0 ml of 0.02 M phosphate buffer—0.14 M sodium chloride—1 mM EDTA solution (pH 7.5) containing about 3 mg of N-[3-(2-pyridyl)dithiopropionyl]-MOM was mixed with 1.0 ml of the abovementioned phosphate buffer containing 4.1 mg of fragment Fab' having 1 thiol group and the mixture was allowed to react to room temperature for 20 hours. The reaction solution was chromatographed on Sephadex G 150 (superfine) column (1.3 cm×95 cm) in physiological saline, as the result of which 5 peaks were found when the absorbance was measured at 280 mm as shown in FIG. 1. The result obtained by the analysis of these peaks according to SDS-PAGE is shown in FIG. 2. In FIG. 2, disc 1 is a pattern of the absorption band of Fab' and disc 2 is that of MOM.

The main component of peak I in FIG. 1 had, as shown by disc 3, molecular weight of about 120,000 and was separated into fragment Fab' (corresponding to disc 1) and MOM (corresponding to disc 2) when reduced with 2 mercaptoethanol. The ratio between them is 2:1. Therefore, the protein of peak 1 is a hybrid consisting of two molecules of fragment Fab' and one molecule of MOM bonded together. The protein of peak II had, as shown by disc 4, molecular weight of about 70,000 and was separated into fragment Fab' and MOM when reduced with 2-mercaptoethanol at the ratio of 1:, as shown by disc 8. Therefore, the protein of peak II is a hybrid consisting of one molecule of fragment Fab' and one molecular of MOM bonded together. The proteins of peaks III and IV are fragment Fab' and MOM respectively both remaining not reacted as shown by discs 5 and 6.

(g) Cytotoxicity of hybrid against L 1210 cells

The cytotoxicity of the protein hybrid obtained in the preceding (f) against the target L 1210 cells was examined.

Figure 3:
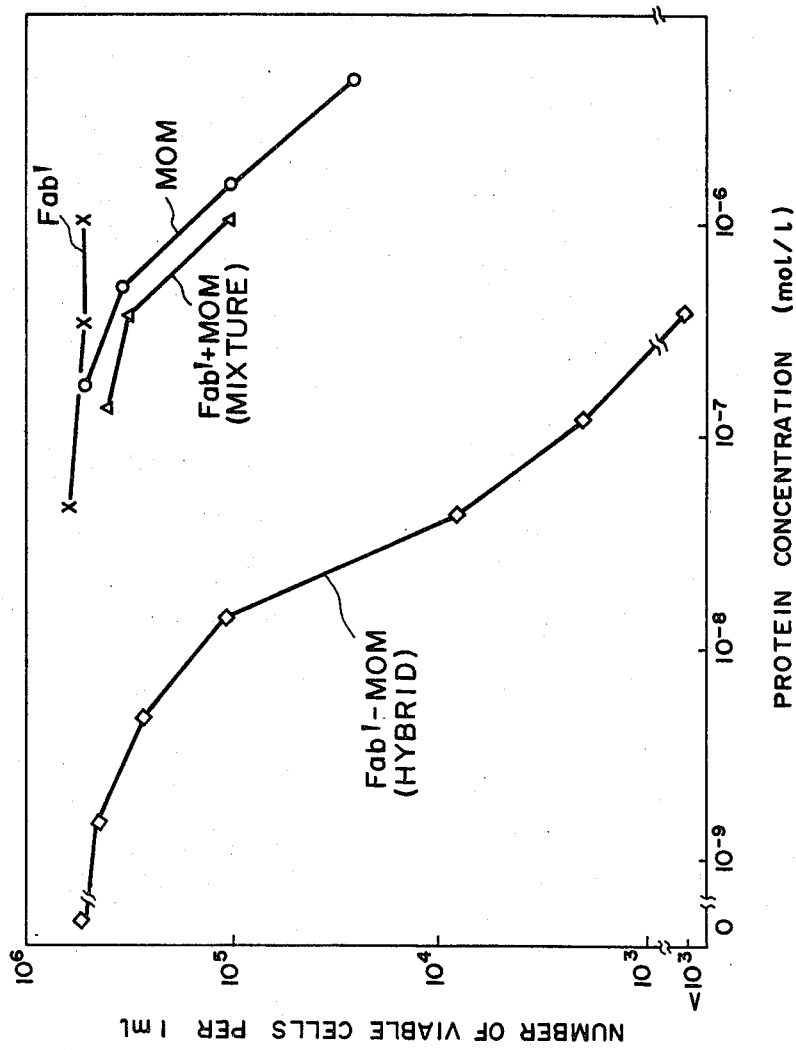
FIG. 3 presents the result of the investigation made on the cytotoxicity of the protein hybrid against L 1210 cells in Example 1, (g), and the graph shows the number of the viable cells after the 42-h incurbation versus concentration of the protein hybrid or its constituent protein added thereto.

0.10 ml of RPMI 1640 culture medium (comprising 10% calf serum, 0.02 mM 2-mercaptoethanol and 0.1 mg/ml of kanamycin) containing $3 \times 10^4$/ml of L 1210 cells was placed in wells of a 96-hole microplate, to which 0.01 ml of subject samples diluted to varied concentrations was added. The culture was carried out at 37° C. in an atmosphere of 5% $CO_2$ for 42 hours and then the viable cells were counted by die exclusion with Trypan Blue. The result: as shown by FIG. 3, Fab', MOM, and a 1:; mixture of them with a protein concentration of $10^{-6}$ moles/liter scarcely showed cytotoxicity. However, the protein hybrid (the protein involved in peak II of FIG. 1) prepared in the preceding (f) showed remarkable cytotoxicity. Incidentally, another experiment showed that the protein hybrid involved in peak I of FIG. 1 had cytotoxicity equal to or somewhat lower than that of the protein hybrid involved in peak II.

EXAMPLE 2

(a) Preparation of MOM having thiol group introduced 2-mercaptoethanol was added to 3.3 ml of 0.1 M tris.hydrochloride—2 mM EDTA (pH 8.3) buffer solution containing 6 mg of N-[3-(2-pyridyl)dithiopropionyl]-MOM in such an amount as to obtain a final concentration of 5 mM. After having been reduced at 37° C. for 1 hour, the reaction solution was put to Sephadex G25 column chromatography equilibrated with an ANE buffer to remove low molecular products, thus giving MOM having about 2 thiol groups on the average.

(b) Preparation of fab' having maleimide group introduced

A mixture consisting of 2.0 ml of ANE buffer containing 8.2 mg of fragment Fab' prepared in Example 1, (e), and 2.0 ml of ANE buffer saturated with o-phenylenedimaleimide was allowed to react at room temperature for 30 minutes. Thereafter, the reaction solution was put to Sephadex G25 column chromatography equilibrated with ANE buffer to remove the reagent remaining unreacted, thus giving fragment Fab' having 1 maleimide group.

(c) Preparation of hybrid by cross-linking MOM having thiol group with fragment fab' having maleimide group A mixture comprising 1.1 ml of ANE buffer containing 2.5 mg of MOM having thiol groups, 2.3 ml of ANE buffer containing 4 mg of fragment Fab' having a maleimide group and 0.34 ml of 0.3 M phosphate buffer—10 mM EDTA (pH 6.5) was allowed to react at 4° C. for 22 hours. The reaction solution was put to the same Sephadex G 150 (superfine) column chromatography as in Example 1, (f), to isolate a hybrid in which Fab' and MOM were linked together at the ratio of 2:1 and a hybrid in which Fab' and MOM were linked together at the ratio of 1:1. Their molecular weight was confirmed by means of SDS-PAGE as in Example 1, (f), and their cytotoxicity against L 1210 cells was confirmed according to the method of Example 1, (g).

EXAMPLE 3

(a) Preparation of MOM having maleimide group introduced 0.03 ml of N,N-dimethylformamide with 7.0 mg/ml metamaleimidobenzoic acid N-hydroxysuccinimide ester dissolved therein was added to 1.0 ml of 0.1 M phosphate buffer (pH 7.0) containing 4.4 mg of MOM prepared according to Example 1, (a), and the mixture was made to react at room temperature for 30 minutes. The reaction solution was then put to Sephadex G 25 column chromatography equilibrated with ANE buffer to remove the unreacted reagent, thus obtaining MOM with a maleimide group introduced.

(b) Preparation of hybrid by cross-linking MOM having maleimide group with fragment Fab' having thiol group 1.0 ml of ANE buffer containing 2.6 mg of MOM having a maleimide group obtained in the preceding (a) and 1.0 ml of ANE buffer containing 4.1 mg of fragment Fab' having a thiol group obtained in Example 1, (e), were mixed and made to react at room temperature overnight. This reaction solution was put to Sephadex G 150 (superfine) column chromatography to isolate a hybrid in which 2 molecules of Fab' and 1 molecule of MOM were linked together and a hybrid in which 1 molecule of Fab' and 1 molecule of MOM were linked together. Several other unidentified hybrids were observed besides these two hybrids.

EXAMPLE 4

(a) Preparation of N-[3-(2-pyridyl)dithiopropionyl]fragment F(ab')$_2$ 0.04 ml of ethanol solution containing 10 mM SPDP was added to 1.2 ml of 0.02 M phosphate buffer—0.14 M sodium chloride—1 mM EDTA (pH 7.5) containing 11.2 mg of fragment F(ab')$_2$ prepared according to Example 1, (d), and the mixture was allowed to react at room temperature for 30 minutes. The reaction solution was subjected to Sephadex G 25 column chromatography equilibrated with the above-mentioned phosphate buffer to remove excess reagent, thus obtaining N-[3(2-pyridyl)dithiopropionyl]-fragment F(ab')$_2$.

(b) Preparation of hybrid by cross-linking N-[3-(2-pyridyl)dithiopropionyl]-fragment F(ab')$_2$ with MOM having thiol group 2.4 ml of 0.02 M phosphate buffer—0.14 M sodium chloride—1 mM EDTA solution (pH 7.5) containing 9.3 mg of N-[3-(2-pyridyl)dithiopropionyl]-fragment F(ab')$_2$ prepared according to the method described in the preceding (a) was mixed with 1.7 ml of ANE buffer containing 3.2 mg of MOM having thiol groups prepared according to Example 2, (a), and the mixture was allowed to react at room temperature for 20 hours. The reaction mixture was put to Sephadex G 150 (superfine) column chromatography according to Example 1, (f), and thus obtained 30th, 31st, and 32nd fractions were pooled together and subjected to SDS-PAGE to obtain the result as shown in FIG. 4. The protein contained in this fraction showed a pattern of bands of disc 3, from which it was observed that it contained a product of about 120,000 molecular weight and a small amount of other products of greater molecular weight besides the material fragment F(ab')₂ (which corresponds to disc 1). The reduction of this protein conducted at 37° C. for 1 hour with 2 mM 2-mercaptoethanol brought about its dissociation into fragment Fab' and MOM (which correspond to disc 2). It was made known from these results that the main product (of about 120,000 molecular weight) was a hybrid comprising fragment F(ab')₂ and MOM linked together by a disulfide bond.

It was also found that this hybrid had somewhat stronger cytotoxicity against L 1210 cells as compared with the hybrid bonded with Fab' obtained in Example 1.

EXAMPLE 5

(a) Fragment F(ab')₂ having maleimide group introduced 0.05 ml of N,N-dimethylformamide with 7.0 mg/ml metamaleimidobenzoic acid N-hydroxysuccinimide ester dissolved therein was added to 1.0 ml of 0.1 M phosphate buffer containing 11.5 mg of fragment F(ab')₂ prepared according to Example 1, (d), and the mixture was made to react at room temperature for 30 minutes. The reaction solution was then put to Sephadex G 25 column chromatography equilibrated with ANE buffer to remove the unreacted reagent, thus obtaining fragment F(ab')₂ with a maleimide group introduced.

(b) Preparation of hybrid by cross-linking F(ab')₂ having maleimide group with MOM having thiol group 2.0 ml of ANE buffer containing 7.6 mg of fragment F(ab')₂ having a maleimide group obtained in the preceding (a) and 1.5 ml of ANE buffer containing 2.7 mg of MOM having a thiol group prepared according to Example 2, (a), were mixed and made to react at room temperature for 24 hours. The reaction mixture was put to Sephadex G 150 (superfine) column chromatography. The absorbance of each fraction was determined at 280 mm and two peaks were observed as in the case of Example 4, (b). When the fraction of the first peak containing a protein of greater molecular weight was subjected to SDS-PAGE, a main product of about 120,000 molecular weight, or a hybrid formed by the linkage of a maleimide group of F(ab')₂ and a thiol group of MOM, was confirmed. The cytotoxicity of the fractions containing this hybrid was inspected according to Example 1, (g), and it was found to have the cytotoxicity against the target cells L 1210.

What is claimed is:

1. A protein hybrid having cytotoxicity prepared by covalently bonding an immunoglobulin, or its fragment, which is capable of binding selectively to an antigen produced by a cell to be killed, to a protein which is obtained from *Momordica charantia* and capable of inhibiting protein synthesis.

2. A protein hybrid having cytotoxicity according to claim 1, which is expressed by the following formula (I) or (II):

Ab—(—(X₁)ₜ—MOM)ₙ  (I)

(Ab—(X₁)ₜ—)ₙMOM  (II)

where Ab indicates an immunoglobulin or its fragment; MOM is a protein which is obtained from *Momordica charantia* and capable of inhibiting protein synthesis; X₁ is a divalent organic group; t indicates 0 or 1; and n represents an integer of 1 to 3.

3. A protein hybrid having cytotoxicity according to claim 1 or 2, which is expressed by the following formula (III) or (IV):

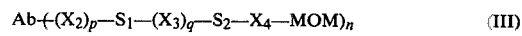

Ab—(—(X₂)ₚ—S₁—(X₃)q—S₂—X₄—MOM)ₙ  (III)

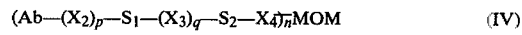

(Ab—(X₂)ₚ—S₁—(X₃)q—S₂—X₄—)ₙMOM  (IV)

where Ab indicates an immunoglobulin or its fragment, MOM is a protein which is obtained from *Momordica charantia* and capable of inhibiting protein synthesis; n represents an integer of 1 to 3; X₂, X₃ and X₄ indicate a divalent organic group respectively; S₁ and S₂ indicate a sulfur atom respectively; and p and q are either the same or different and represent 0 or 1.

4. A protein hybrid having cytotoxicity according to claim 1 or 2, which is expressed by the following formula (V) or (VI):

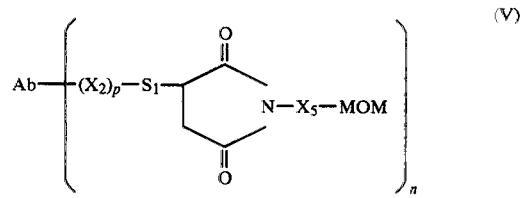

(V)

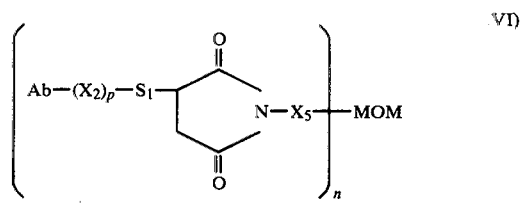

(VI)

where Ab indicates an immunoglobulin or its fragment; MOM is a protein which is obtained from *Momordica charantia* and capable of inhibiting protein synthesis; n represents an interger of 1 to 3; X₂ indicates a divalent organic group; S₁ indicates a sulfur atom; and p is 0 or 1; and X₅ indicates a divalent organic group.

5. A process for preparing a protein hybrid having cytotoxicity expressed by the following formula (III-1) or (IV-1):

Ab—(—(X₂)ₚ—S₁—S₂—X₄—MOM)ₙ  (III-1)

(Ab—(X₂)ₚ—S₁—S₂—X₄—)ₙMOM  (IV-1)

where Ab indicates an immungloublin or its fragment; MOM is a protein which is obtained from *Momordica charantia* and capable of inhibiting protein synthesis; n represents an integer of 1 to 3; X₂ and X₄ indicate a divalent organic group, respectively; S₁ and S₂ indicate a sulfur atom respectively; and p represents 0 or 1; comprising reacting a disulfide group, which is introduced into one of the protein of an immunoglobulin or its fragment and the protein which is obtained from *Momordica charantia* and is capable of inhibiting protein synthesis with a thiol group which is either self-produced in or introduced into the other of said proteins.

6. A process for preparing a protein hybrid having cytotoxicity expressed by the following formula (III-2) or (IV-2):

$$Ab\text{--}((X_2)_p\text{--}S_1\text{--}X_3\text{--}S_2\text{--}X_4\text{--}MOM)_n \quad \text{(III-2)}$$

$$Ab\text{--}((X_2)_p\text{--}S_1\text{--}X_3\text{--}S_2\text{--}X_4)_n MOM \quad \text{(IV-2)}$$

wherein Ab indicates an immunoglobulin or its fragment; MOM is a protein which is obtained from *Momordica charantia* and capable of inhibiting protein synthesis; n is an integer of 1 to 3; $X_2$, $X_3$ and $X_4$ indicate a divalent organic group respectively; $S_1$ and $S_2$ indicate a sulfur atom respectively; and p is 0 or 1; comprising linking an immunoglobulin or its fragment, which has a thio group either self-produced therein or introduced thereto, with a protein, which is obtained from *Momordica charantia*, capable of inhibiting protein synthesis, and has a thiol group introduced thereto, using a cross-linking agent having two functional groups capable of reacting with thiol groups.

7. A process for preparing a protein hybrid having cytotoxicity expressed by the following formula (V) or (VI):

$$Ab\text{--}\left[(X_2)_p\text{--}S_1\text{--}\underset{\underset{O}{\|}}{\overset{\overset{O}{\|}}{\diagup\diagdown}}N\text{--}X_5\text{--}MOM\right]_n \quad \text{(V)}$$

$$Ab\text{--}\left[(X_2)_p\text{--}S_1\text{--}\underset{\underset{O}{\|}}{\overset{\overset{O}{\|}}{\diagup\diagdown}}N\text{--}X_5\right]_n\text{--}MOM \quad \text{(VI)}$$

where Ab indicates an immunoglobulin or its fragment; MOM is a protein which is obtained from *Momordica charantia* and capable of inhibiting protein synthesis; $X_2$ indicates a divalent organic group; $X_5$ indicates a divalent organic group; $S_1$ indicates a sulfur atom; and p is 0 or 1; comprising reacting an immunoglobulin or its fragment having a thiol group either self produced therein or introduced thereto with a protein which is obtained from *Momordica charantia*, capable of inhibiting protein synthesis, and has a maleimide group introduced thereto.

* * * * *